(12) United States Patent
de Oliveira

(10) Patent No.: US 7,207,357 B2
(45) Date of Patent: Apr. 24, 2007

(54) MULTIFUNCTIONAL PLIERS TOOL

(76) Inventor: João Bosco de Oliveira, Rna Proressor Alexandre Correia, 370, Apto. 71, Morumbi, São Paulo (BR) 05657-230

(*) Notice: Subject to any disclaimer, the term of this patent is extended or adjusted under 35 U.S.C. 154(b) by 0 days.

(21) Appl. No.: 11/210,241

(22) Filed: Aug. 23, 2005

(65) Prior Publication Data
US 2006/0272730 A1  Dec. 7, 2006

(30) Foreign Application Priority Data
Jun. 6, 2005 (BR) .................................. 0502209

(51) Int. Cl.
*B21F 9/02* (2006.01)
(52) U.S. Cl. ................... 140/93.2; 140/123.6
(58) Field of Classification Search ............ 140/123.6, 140/93.2, 93.4, 152, 150; 81/9.3; 24/23 R, 24/16 PB; 100/30, 32, 33 R
See application file for complete search history.

(56) References Cited
U.S. PATENT DOCUMENTS
5,137,060 A * 8/1992 Wolcott .................. 140/123.6
5,193,254 A * 3/1993 Geisinger ..................... 24/484
5,372,166 A * 12/1994 Lai .......................... 140/123.6
5,507,206 A * 4/1996 Solski ........................ 81/9.3

* cited by examiner

*Primary Examiner*—Lowell A. Larson
*Assistant Examiner*—Debra Wolfe
(74) *Attorney, Agent, or Firm*—Christopher & Weisberg, P.A.

(57) ABSTRACT

A multifunctional pliers tool to fit clamp-type products, with its unique characteristic to be possibly applied to several application fields, such as building construction and also medicine field, where it achieves aggregating at the same product one application function; a tensioning function; a cutting function and a finishing function, and to get that a multifunctional pliers product was developed and is composed by a right lever component; a left lever component; a tension regulator pin component; a fitting cylinder component; and an assembly pin component, being in particular its functional concept is understood by the segmentation in four steps: the first one named clamp application; the second step named clamp tensioning; the third step named clamp folding and the fourth step named clamp segment cutting with finishing of the obtained edges.

3 Claims, 8 Drawing Sheets

MULTIFUNCTIONAL PLIERS TOOL

FIELD OF THE INVENTION

The present invention is in the field of tools with several functions

BACKGROUND OF THE INVENTION

The state-of-art of tools destined to join two separated parts of one or more objects has in the figure of pliers product its better representation, and may be defined as a kind of pincers or tongs, adequate to support, to fasten or to cut objects, with core constructive concept of two lever components of iron or steel that spin around an axis and with smooth or knurled edges, which may be plain, bent, cylindrical or in a bridge.

This classical definition of pliers product presents limitations of use, since the support function is not dynamic, it is to say, once the object is supported there is any kind of tension action, at least in an adequate way, making its use in the application of clamp elements be non-practicable from the point of view of agility and final quality of application, mainly when this application is of medical nature. In a similar way, when the cutting function is performed, the necessary movement to keep tension presents handling difficulties, increasing the execution time of the cutting operation.

However, ergonomics have received special attention since the 90's when the technological advance in several areas has experienced an original evolution with several new product launches. In the same way, the ergonomics analysis has become very important in different fields. The ergonomics must not be limited of the product being evaluated but all that involve the ergonomics conditions in operational procedures. The demand for new products is calling for a more productive efficiency, especially for assembling and finishing of vehicles and building constructions, as edifices, bridges and others, in a very wide scope.

The operational ergonomic study also includes ergonomics study applied to surgical procedures, where a medical team is in a work limit condition, being time a constantly controlled parameter. In this context the practical experience is the shorter way to identify the need of adapted tools to the adverse conditions specific of this work environment.

In the present invention it is found that the medical field, more specifically in the surgical procedures, it is one or the most valuable fields to aggregate value to the finishing of these procedures. Finishing should be understood as the restoring procedure of the affected structures.

In the present invention a constructive arrangement is introduced in tools with multiple functions, especially pliers, and it is intended to assist or facilitate the fixing of metallic clamp-type elements. The present invention is intended to be an ergonomic tool during application, traction, folding, cutting and finishing for joining together the edges of clamp-type elements. It is particularly applied to metallic clamp elements for joining two or more parts of piece or object, being this joining applied with a significant traction force in order to get high stable and reliable condition.

SUMMARY OF THE INVENTION

This application seeks to provide a multifunctional pliers comprising: (a) a right lever (A); (b) a left lever (B) attachable to the right lever component (A); (c) a tension regulator pin (C); (d) a fitting cylinder (D), and (e) an assembly pin ( joint.

This application also seeks to provide a method of using the multifunctional pliers according to this invention with a clamp comprising a main body (2A) having a first and a second edge, the first edge having a first groove area (2C) and the second edge having a second groove area (2D), comprising the steps of: (I) applying the clamp; (II) tensioning the clamp; (III) folding the clamp, and (IV) cutting the clamp segment and finishing of obtained edges.

Figure 1:
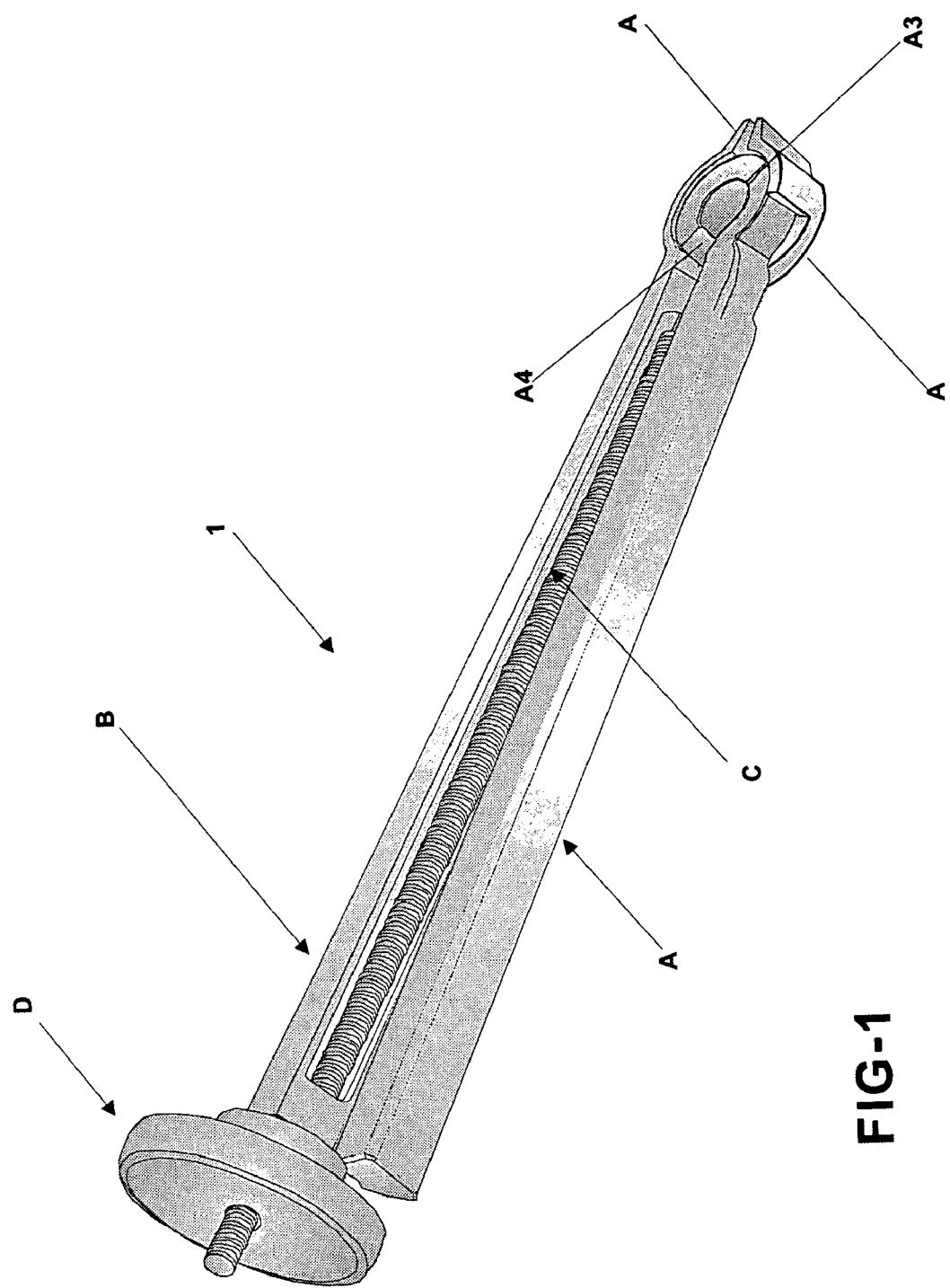
FIG. 1 shows a perspective view of the multifunctional pliers.

The following detailed description must be referred to the drawings above, which are highly schematic ones, representing a way of selected realization but not limiting the scope of this invention, this one only limited to the stated in the claiming statement.

DETAILED DESCRIPTION OF THE INVENTION

The multifunctional pliers tool of this invention provides ergonomics to the jointing operation between element parts. The performance of the mentioned operation will have a substantial reduction of time, fundamental in cases where this parameter is defined as critical. One example of such a situation is during surgical procedures, where it is crucial and some times necessary that the procedures to be performed as quickly as possible to avoid or reduce the risk of a hospital infection.

The mentioned aggregated value may be translated, for example in the cardiac area, by obtaining a special condition of operational ergonomics when closing the osseous structure known as "sternum", since this intervention is considered very aggressive.

The above mentioned favorable operational ergonomics must be understood as the facility or help found by the individual to precede the fastening of the "sternum" bone with special clamp elements, mainly made of high-resistant metallic alloys, since this procedure requires at least a set of four clamps.

The differentiation of surgical procedure obtained by the mentioned operational ergonomics is possible due to an original constructive concept and consequent functional concept applied in the multifunctional pliers, where an edge of the clamp element is fitted to a special head designed to this product in a way that, after this fitting, such edge be fitted to a tension regulator pin.

When this tension regulator pin is distanced from the special head, the clamp element is tensioned in a way to act as a jointing element between two previously separated parts. When the desired fitting is obtained, the operator acts manually over the clamp element, bending it at the same region of the special head and pressing the pair of levers. This movement starts the cutting function, separating from the body of the clamp element the unused segment.

The finishing between the jointed edges of the clamp element may also be made through the intervention over the nozzle of a special head over them, resulting in a reliable and qualified jointing procedure. These procedures occur in an agile way, where in no situation the operator (subject) looses the operation control with the multifunctional pliers, This will ensure that the operator has total control over the clamp application to the effective jointing of the edges, providing great agility and minimizing his/her stress, decreasing human errors due to physical and/or mental fatigue.

The multifunctional pliers of this invention may be applied to any kind of jointing of distinctive parts that uses clamp, with special use in cases with high-tension application, as well as reduced time of operation.

The pliers of this invention may be used in many different fields and have many different uses. The pliers is useful in several sectors such as building construction, automotive, electric-electronic, with particular importance in medicine, more specifically on surgical procedures at the end of invasive surgical procedures requiring a fast restoring procedure of affected structures.

As seen in FIG. 1, the multifunctional pliers tool (1) of the present invention includes a right lever (A), including an extruded linear lever (A1). Alternatively, the pliers further include a quadratic transversal section, in order to provide support to a cutting force application (Fc).

The upper edge of the extruded linear profile (A1) includes a semi-cylindrical assemblage (A2), with structured wall, whose primary function is to provide attachment of the right lever component (A) to the left lever component (B), forming a rotation axis.

Figure 2:
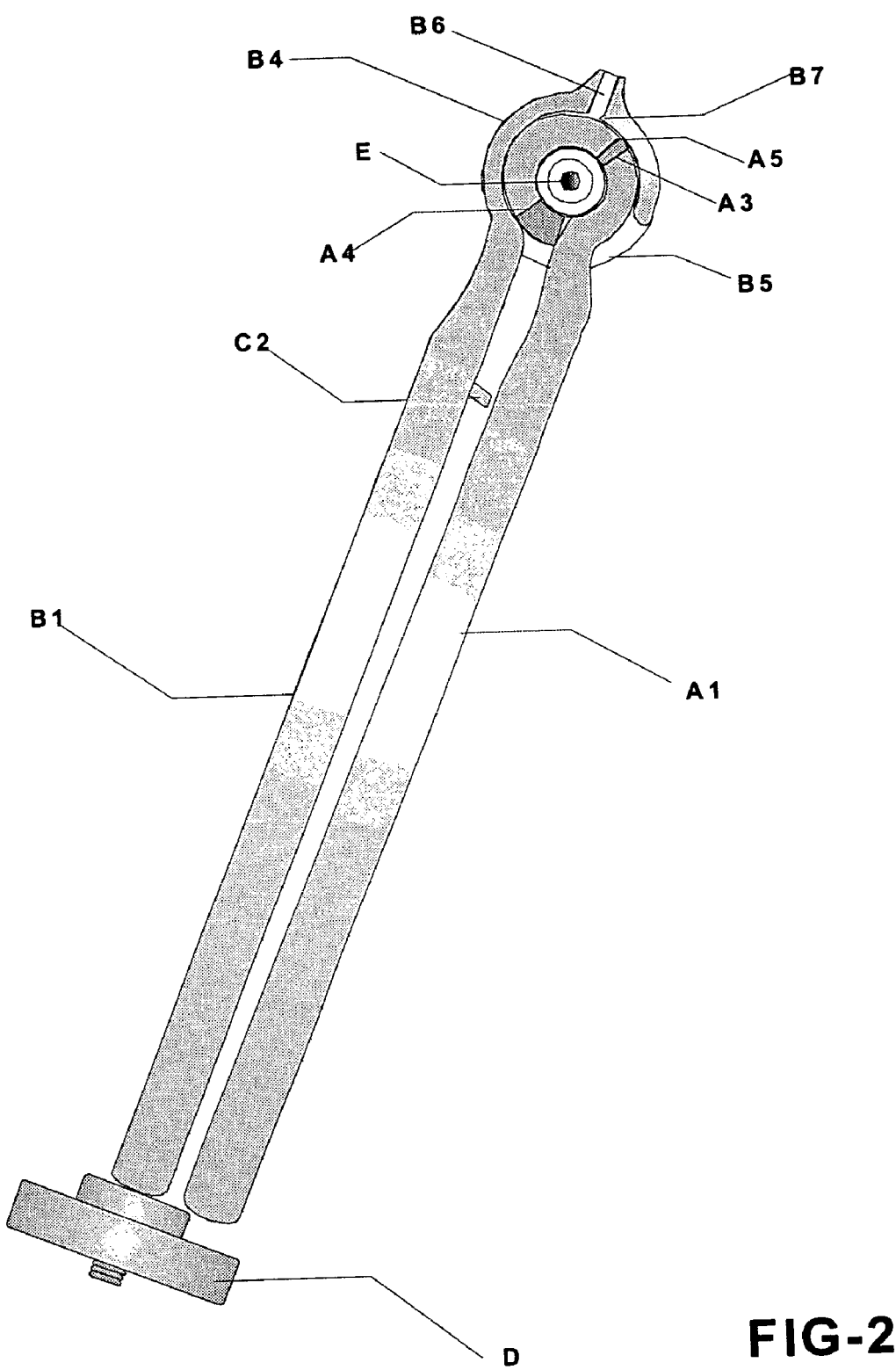
FIG. 2 shows a perspective view of the multifunctional pliers.
Figure 6:
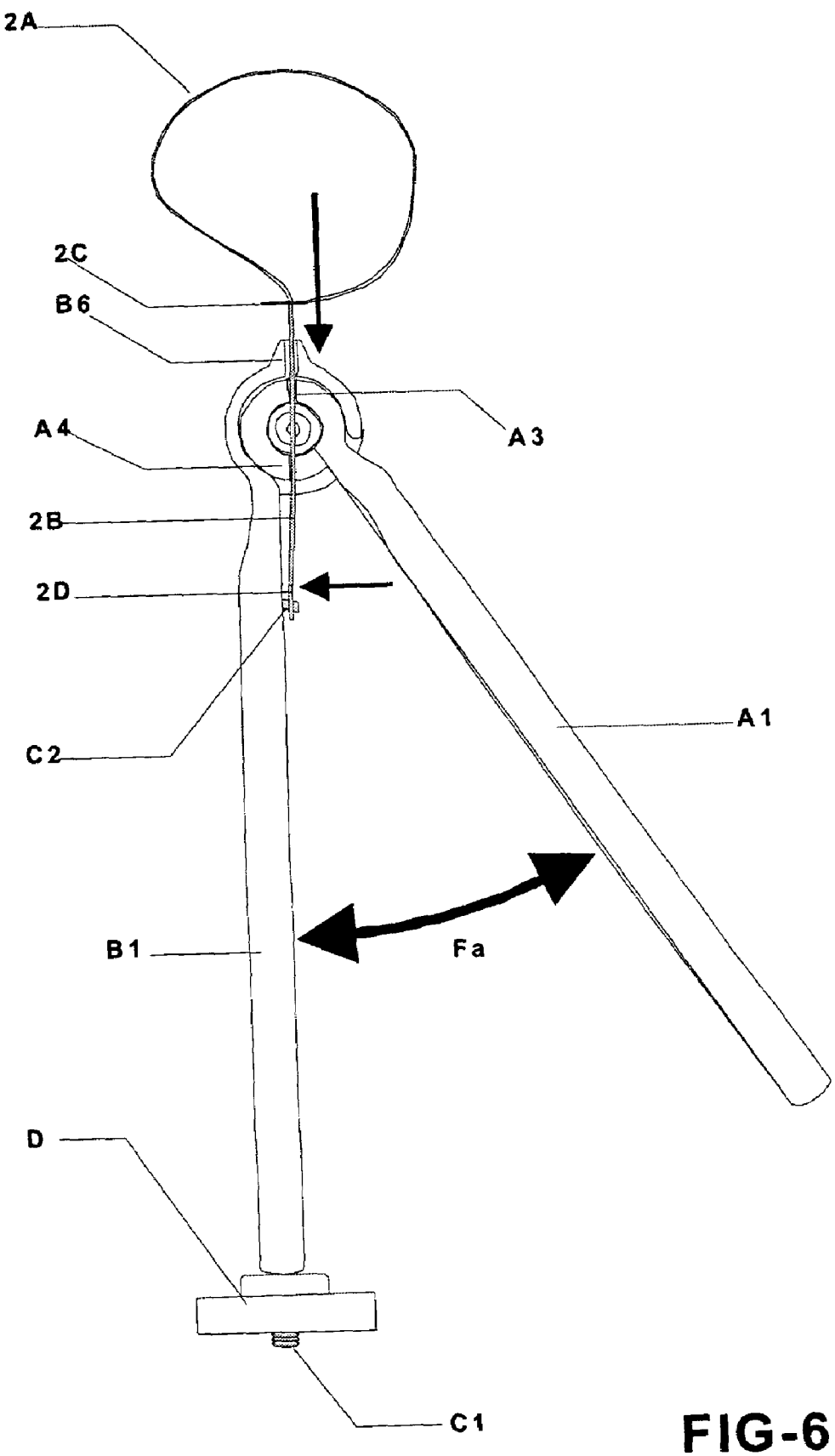
FIG. 6 shows the step of clamp application with the use of the multifunctional a pliers.

As seen in FIGS. 1, 2 and 6 the semi-cylindrical assemblage (A2) includes an opening (A3), whose function is to provide the application of the segment (2B) of the clamp (2) to be tensioned.

An alignment wall (A4) is provided to define a semi-cylindrical edge of the semi-cylindrical assemblage (A2), whose main function is to provide alignment to the segment to be tensioned (2B).

The opening (A3) of the semi-cylindrical assemblage (A2), includes a first resilient component (A5) in a tooth shape to facilitate the cutting of the segment to be tensioned (2B), is it can be seen in FIG. 2.

Figure 3:
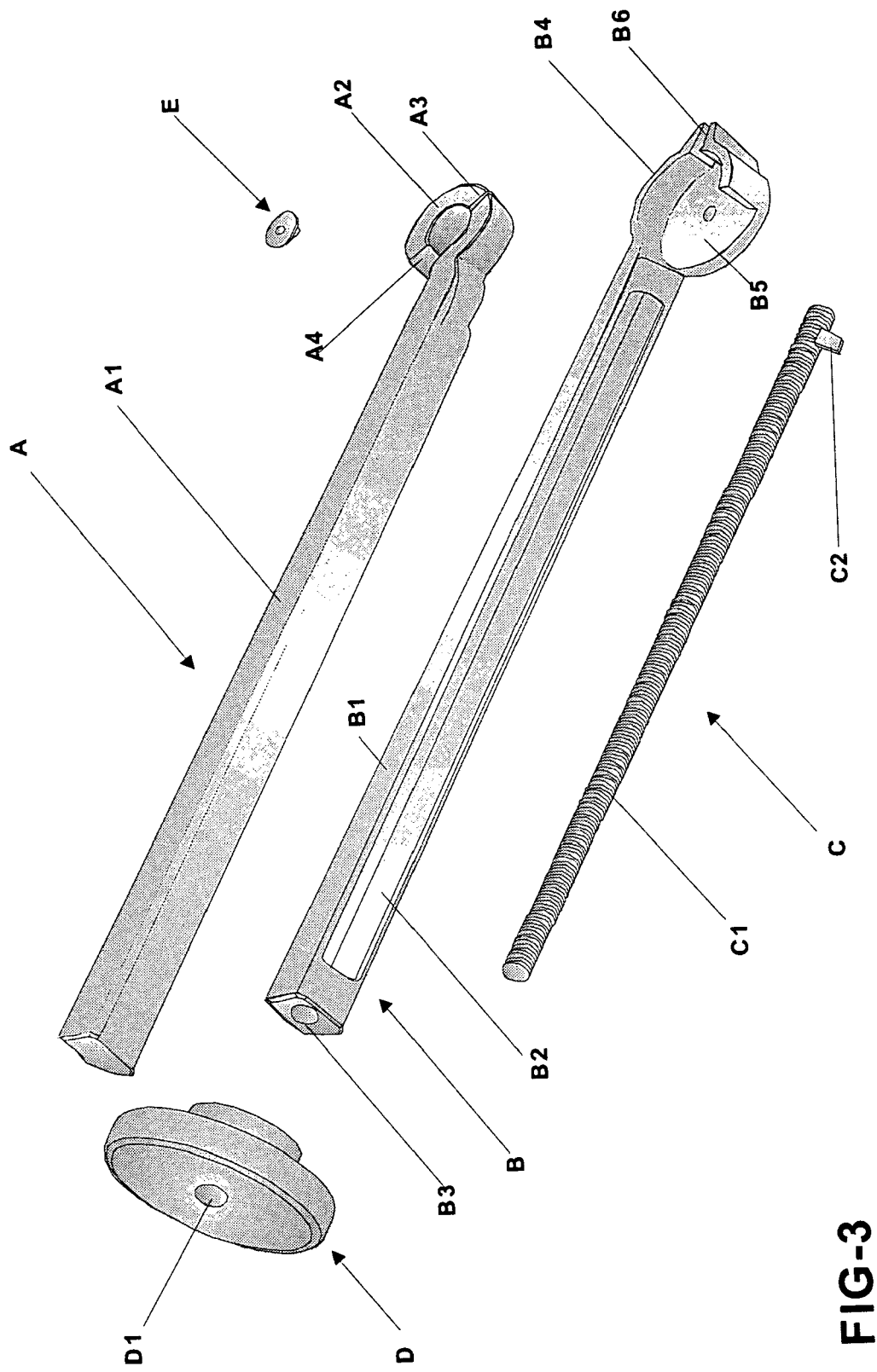
FIG. 3 shows an exploded view of the multifunctional pliers.

FIG. 3 shows the left lever, which includes an extruded linear profile (B1), presenting a housing (B2) in an internal side, whose function is to provide the necessary assembling and structure to the tension regulator pin (C) which is the thread component of tension force. The lower (inferior) edge of left lever (B) includes a thread hole (B3), whose function is to enable the threaded movement of the tension regulator pin (C).

At the upper extreme edge of the extruded linear profile (B1) it is defined a head (B4) also in a semi-cylindrical shape, being supported by a circular basis (B5), whose function is to receive the semi-cylindrical assemblage (A2). An access nozzle (B6) including an opening formation in the central portion is attached to the head (B4) to provide the application of the segment to be tensioned (2B) through the opening (A3) of the semi-cylindrical assemblage (A2) of the right lever (A), as seen in FIG. 6.

At the right internal portion of the opening (A3), it is defined a second resilient component (B7) also in a tooth shape to facilitate the cutting of the segment to be tensioned (2B) acting in a concurrent way with the first resilient component (A5) also provided in the internal part of the opening (A3) in the semi-cylindrical assemblage (A2) of the right lever (A).

The tension regulator pin (C) is assembled through a linear axis (C1), including a threaded formation and groove resilient component (C2), in an upper portion to provide an adequate groove to a posterior tension force of the segment to be tensioned (2B).

The tension regulator pin component (C), is assembled in an inner side of the housing (B2), and includes a thread in a lower portion which is threaded to the threaded the first opening (B3). The fitting cylinder component (D) is also threaded to the central opening (D1), enabling the manual fitting of tension force of the segment to be tensioned (2B).

An assembling pin (E) is provided for the assembly of the right lever (A) and left lever (B).

Figure 4:
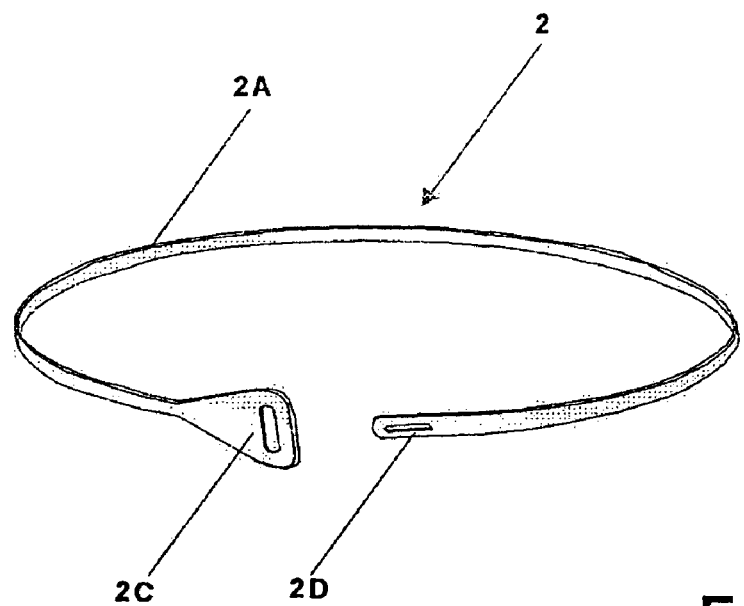
FIG. 4 shows a perspective view of a clamp in an open position used with the multifunctional pliers.

FIG. 4 shows a clamp (2) to be used with the multifunctional pliers, in an open position, including a main body (2A) having a first and a second edge. The first edge having a first groove area (2C) and the second edge having a second groove area (2D).

Figure 5:
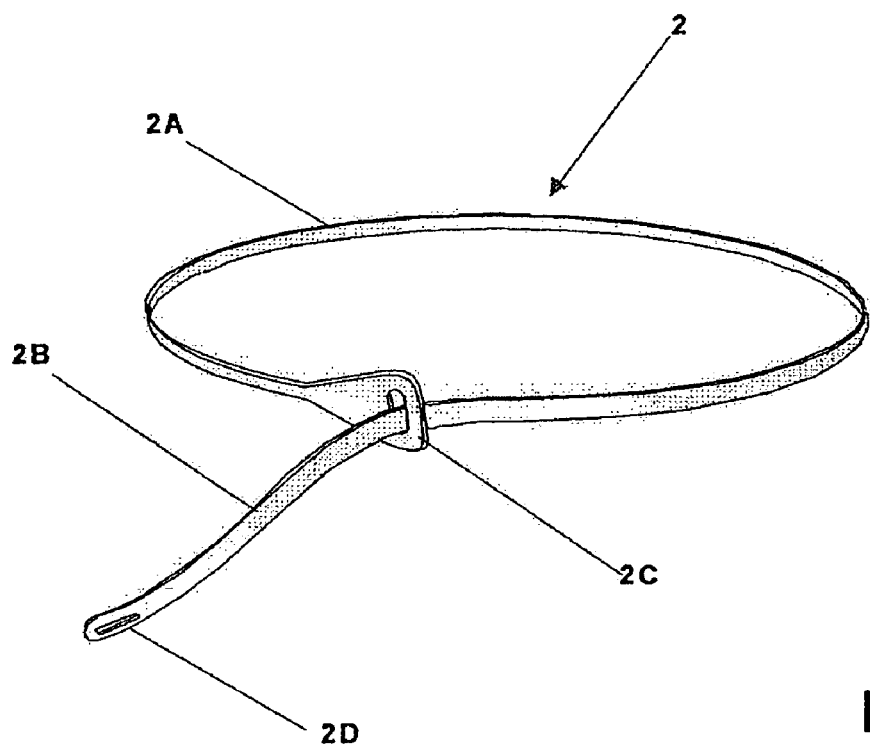
FIG. 5 shows a perspective view of a clamp in a closed position used with the multifunctional pliers.

FIG. 5 shows a clamp (2) assembly where the second groove area (2D) passes through the first groove area (2C), thus creating a segment to be tensioned (2B).

The method of using of the multifunctional pliers is shown in detail in FIGS. 6, 7, 8 and 9. The method is a method of using the multifunctional pliers with a clamp comprising a main body (2A) having a first and a second edge, the first edge having a first groove area (2C) and the second edge having a second groove area (2D), comprising the steps of:
  (i) applying the clamp to the pliers;
  (ii) tensioning the clamp;
  (iii) folding the clamp, and
  (iv) cutting the clamp segment and finishing of obtained edges.

The first step, the clamp application, implies the total opening between the right lever (A) and left lever (B) by means of an opening force (Fa), as shown in FIG. 6. The segment to be tensioned (2B) is then applied to the opening space (A3) of right lever (A) and existent opening in the access nozzle (B6) of left lever component (B), being the second groove area (2D) of clamp (2) incased to the groove resilient component (C2).

In this step it is possible to check that besides the alignment between opening (A3) of right lever (A) and of the existent opening in the access nozzle (B6), there is also a natural alignment of the alignment wall (A4).

Figure 7:
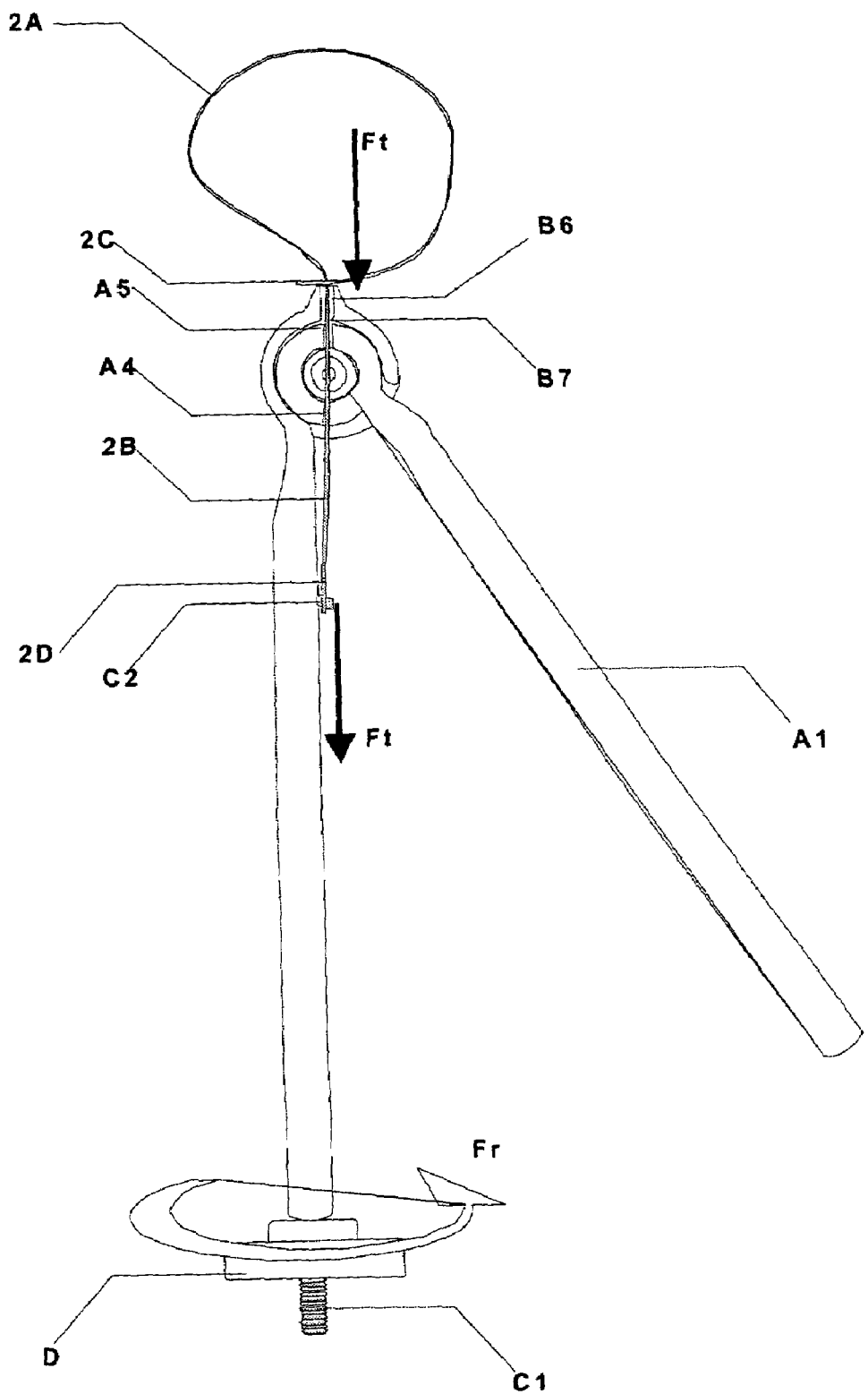
FIG. 7 shows the tension force step of clamp with the use of the multifunctional pliers.

The second step, the clamp tensioning as shown in FIG. 7, implies the beginning of the tensioning of the segment to be tensioned (2B), by means of application of a rotation (Fr) of the fitting cylinder component (D), leading the linear axis (C1) to dislocate outside the housing (B2), by means of a tension force (Ft) created due to the interference between the resilient component (C2) and the second groove area (2D), adequately fastening the main body (2A) to the parts to be joined.

Figure 8:
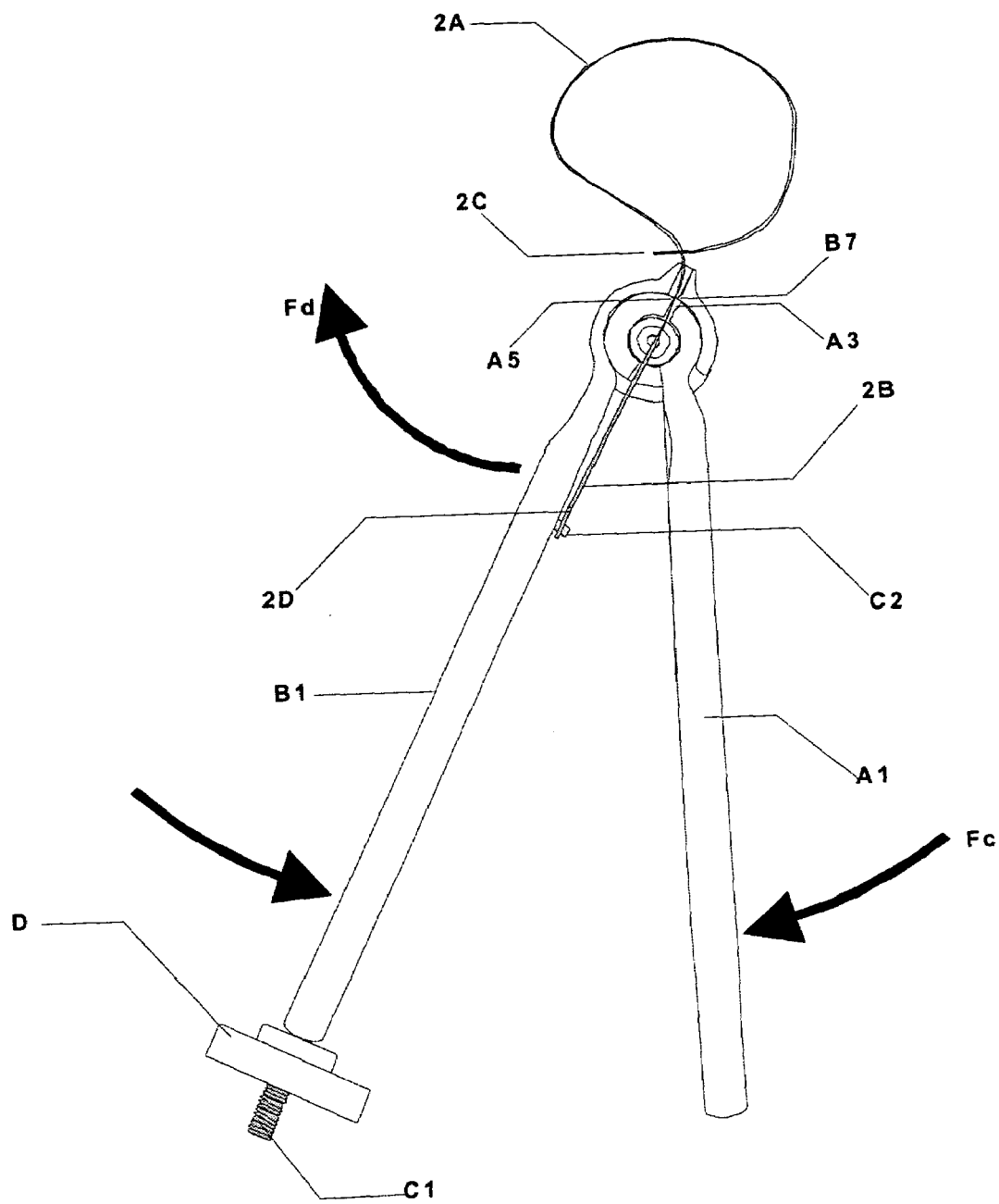
FIG. 8 shows the clamp bending step with the use of the multifunctional pliers.

The third step, the clamp folding as shown in FIG. 8, begins when a folding force (Fd) is applied to the multifunctional pliers (1), from a left side.

The fourth step, the clamp segment cutting, begins when a cutting force (Fc) is applied to move the right lever (A) towards the left lever (B), dislocating the opening position (A3) in relation to the opening of the access nozzle (B6), cutting off the segment to be tensioned (2B). The cutting is facilitated by the action of the first resilient component (A5) and second resilient component (B7).

Figure 9:
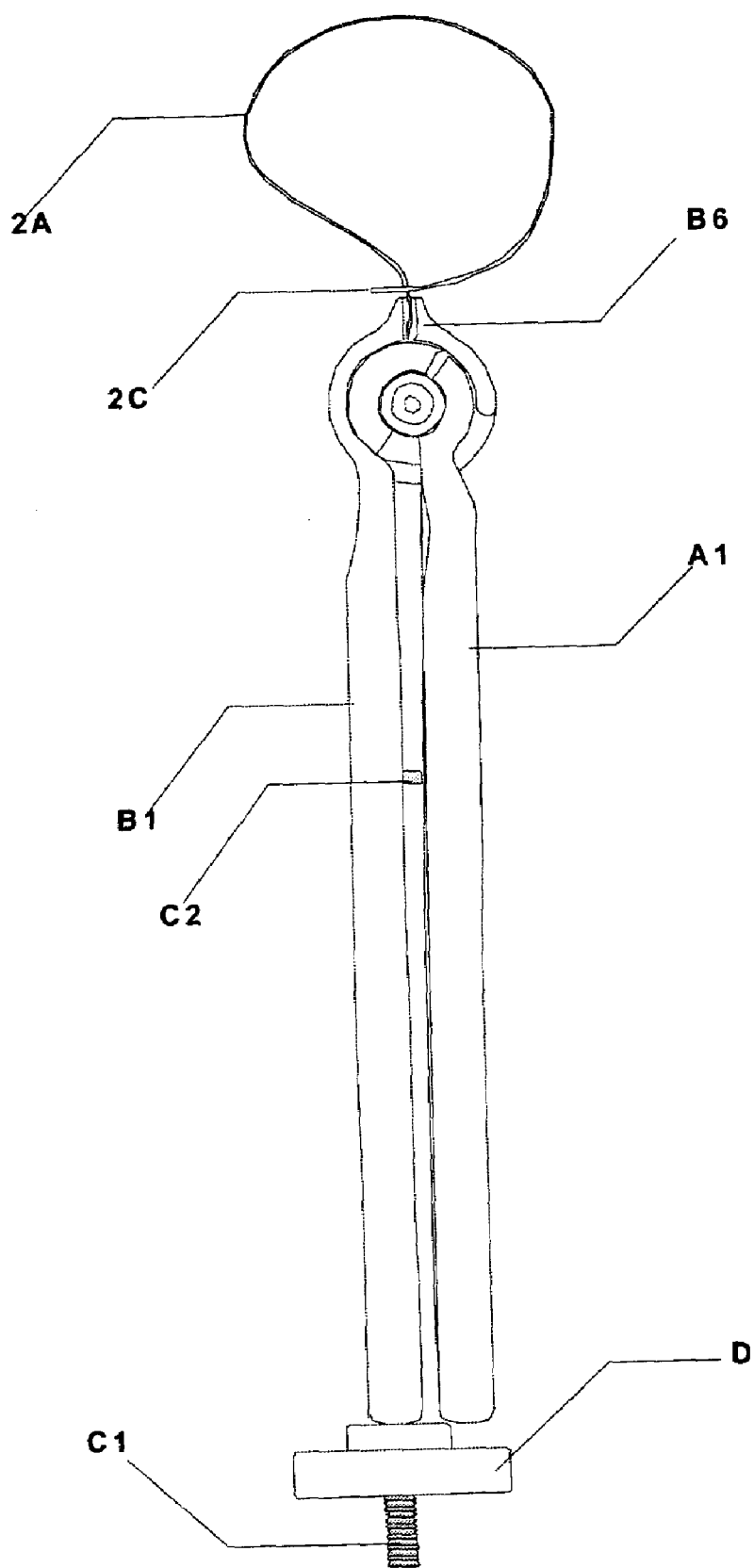
FIG. 9 shows the clamp cutting step with the use of multifunctional pliers.

FIG. 9 shows the final position obtained between right lever (A) and left lever (B). Here the linking between the edges of the clamp (2) are completed and better finished, by means of using the structure of the access nozzle element (B6), thus getting a better quality fastening.

The invention claimed is:

1. A multifunctional pliers comprising in combination:
   (a) a right lever;
   (b) a left lever attachable to the right lever component;
   (c) a tension regulator pin;
   (d) a fitting cylinder; and
   (e) an assembly pin providing the assembly of the right lever and left lever forming a rotation axis,
   wherein the components are arranged to provide an ergonomics operation in procedures of separated parts joint, and
   wherein the right lever includes an extruded linear lever including a semi-cylindrical assemblage including at least one edge, a structured wall forming an opening: the semi-cylindrical assemblage limited in one edge by an alignment wall; and the semi-cylindrical assemblage including a first resilient component in a tooth shape in complement to the opening, and
   wherein the left lever includes an extruded linear lever including a housing in an internal side, a lower edge having a thread hole, an upper edge defining a head in a semi-cylindrical shape and supported by a circular basis, and an access nozzle, the access nozzle including an opening with an internal portion and a central portion, the central portion attached to the head, and the internal portion defining a second resilient component in a tooth shape, and
   wherein the tension regulator pin is assembled through a linear axis, including a threaded formation and a groove resilient component, in an upper portion.

2. A method of using the multifunctional pliers according to claim 1 with a clamp comprising a main body having a first and a second edge, the first edge having a first groove area and the second edge having a second groove area, comprising the steps of:
   (i) applying the clamp to the pliers by implying a total opening between the right lever and left lever by means of an opening force, a segment to be tensioned is then applied to the opening of the right lever and existent opening in an access nozzle of the left lever component, wherein the second groove area of clamp is incased to a groove resilient component, located in an upper portion of the tension regulator pin;
   (ii) tensioning the clamp by tensioning the segment to be tensioned, by means of application of a rotation of a fitting cylinder, leading a linear axis to dislocate outside a housing in an internal side of the left lever, by means of a tension force created due to the interference between a groove resilient component, located in an upper portion of the tension regulator pin and the second groove area adequately fastening the main body to parts of a target object to be joined;
   (iii) folding the clamp by applying a folding force to the multifunctional pliers, from a left side, and
   (iv) cutting the clamp segment and finishing of obtained edges by applying a cutting force moving the right lever towards the left lever, dislocating an opening position in the right lever in relation to the opening of an access nozzle, including an opening with an internal portion and a central portion, the central portion attached to a head of the left lever; cutting off the segment to be tensioned.

3. The method of using the multifunctional pliers according to claim 2, wherein the cutting of the segment to be tensioned is facilitated by the action of a first resilient component in the right lever and a second resilient component the left lever.

* * * * *